United States Patent [19]

Rasberger

[11] 3,971,757

[45] July 27, 1976

[54] 3-ALKYL-4-OXO-IMIDAZOLIDINES AND THEIR 1-OXYLS

[75] Inventor: Michael Rasberger, Allschwil, Switzerland

[73] Assignee: Ciba-Geigy Corporation, Ardsley, N.Y.

[22] Filed: June 5, 1974

[21] Appl. No.: 476,365

[30] Foreign Application Priority Data

June 22, 1973 Switzerland.......................... 9185/73

[52] U.S. Cl........................... 260/45.8 N; 260/309.7
[51] Int. Cl.²..................... C08K 5/00; C07D 49/34
[58] Field of Search..................... 260/309.7, 45.8 N

[56] References Cited
UNITED STATES PATENTS

| | | | |
|---|---|---|---|
| 3,205,195 | 9/1965 | Cook ........................... | 260/309.7 X |
| 3,448,074 | 6/1969 | Kitaoka et al. .............. | 260/309.7 X |
| 3,532,703 | 10/1970 | Murayama et al. .......... | 260/309.7 X |
| 3,645,965 | 2/1972 | Murayama et al. ............ | 260/45.8 N |
| 3,769,259 | 10/1973 | Chalmers........................... | 260/45.8 |

FOREIGN PATENTS OR APPLICATIONS

| | | | |
|---|---|---|---|
| 3,769M | 12/1965 | France............................... | 260/309.7 |
| 46-2905 | 1/1971 | Japan.............................. | 260/45.8 N |
| 1,202,299 | 8/1970 | United Kingdom.............. | 260/309.7 |

*Primary Examiner*—Ethel G. Love
*Attorney, Agent, or Firm*—Nestor W. Shust

[57] ABSTRACT

2,2,5,5-Tetraalkyl- and 2,5-Dispiroalkylene-4-oxoimidazolidines which are substituted in 3-position by mono- to tetravalent radicals, are exellent light-stabilizers for organic polymers. They possess a higher compatibility with organic polymers than the corresponding imidazolines unsubstituted in 3-position, from which they may synthesized by reactions known for N-substitution. The preferred substituents in 3-position are alkyl, alkylene, alkenyl, aralkyl and esteralkyl groups.

The 1-nitroxyls derived from the imidazolidines by oxidation with hydrogen peroxide or percarboxylic acids too are good light stabilizers.

12 Claims, No Drawings

3-ALKYL-4-OXO-IMIDAZOLIDINES AND THEIR 1-OXYLS

The invention relates to new derivatives of 4-oxo-imidazolidine, a process for their manufacture, their use as light stabilizers for organic polymers and the polymers stabilised with these compounds.

The new compounds correspond to the formula I

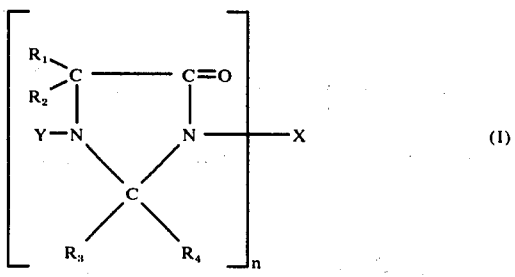

wherein $R_1$, $R_2$, $R_3$ and $R_4$ independently of one another each denote an alkyl group or $R_1$ and $R_2$ and/or $R_3$ and $R_4$ together with the C atom to which they are bonded form a cycloalkyl radical, Y denotes hydrogen or the oxyl radical-O., $n$ denotes an integer from 1 to 4 and X, if $n$ is 1, denotes an alkyl group which can be substituted by groups containing O, N or S, an alkenyl, alkinyl or aralkyl group or an aralkyl group substituted by hydroxyl or ester groups, if $n$ is 2, an alkylene group which can be interrupted by O, NH or S or by groups containing O, N or S, or an alkenylene, alkinylene or bis(alkylene)arene group, if $n$ is 3, a group

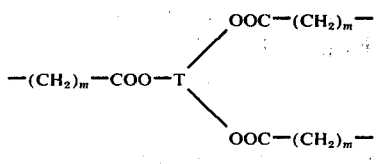

in which $m$ represents a number form 1 to 4 and T represents a trivalent hydrocarbon radical, and if $n$ is 4, a group

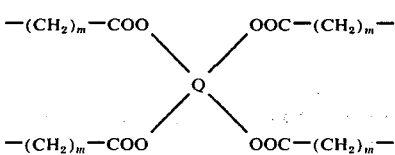

in which $m$ represents a number from 1 to 4 and Q represents a tetravalent hydrocarbon radical, and their salts with organic or inorganic acids.

If $R_1$, $R_2$, $R_3$ and $R_4$ denote an alkyl group, this can be, for example, methyl, ethyl, n-propyl, iso-propyl, n-butyl, tert.-butyl, n-amyl, sec.-amyl, n-octyl, n-decyl, n-dodecyl, n-tetradecyl, n-hexadecyl or n-octadecyl.

If $R_1$ and $R_2$, or $R_3$ and $R_4$, together with the C atom to which they are bonded form a cycloalkyl ring, this can be, for example, a cyclopentyl, cyclohexyl or cyclooctyl ring.

If $n = 1$, X can denote alkyl groups, such as, for example, methyl, ethyl, n-propyl, iso-propyl, n-butyl, n-hexyl, n-octyl, n-decyl, n-dodecyl, n-tetradecyl, n-hexadecyl or n-octadecyl.

If X is an alkyl group substituted by groups containing O, N or S, X can be, for example, the following groups: hydroxyalkyl such as $-CH_2CH_2OH$ or $-CH_2CHOH-CH_3$; carboxyalkyl such as $-CH_2COOH$; alkyl substituted by ester groups, for example alkoxycarbonylalkyl such as $-CH_2COOCH_3$, $-CH_2COOC_2H_5$, $-CH_2COOC_8H_{17}$, $-CH_2COOC_{12}H_{25}$ or $-CH_2COOC_{18}H_{37}$, or alkylcarbonyloxyalkyl such as $-CH_2CH_2OOCCH_3$, $-CH_2CH_2OOCC_7H_{15}$, $-CH_2CH_2OOCC_{11}H_{23}$, $-CH_2CH_2OOCC_{17}H_{35}$ or

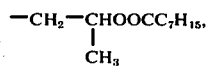

or arylcarbonyloxyalkyl such as

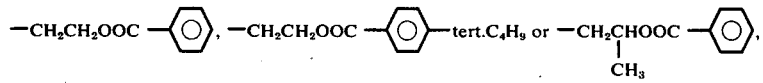

or cycloalkylcarbonyloxyalkyl such as

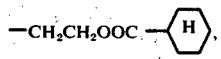

or aralkylcarbonyloxyalkyl such as

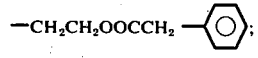

amidoalkyl such as alkylcarbonylaminoalkyl, for example $-CH_2CH_2NHCOCH_3$, $-CH_2CH_2NHCOC_{17}H_{35}$ or $-CH_2CH_2CH_2NHCOC_7H_{15}$, or carbamoylalkyl such as $-CH_2CONH_2$ or $-CH_2CH_2CONH_2$, or alkylaminocarbonylalkyl such as $-CH_2CONHC_2H_5$ or $-CH_2CH_2CONHC_{12}H_{25}$, or arylaminocarbonylalkyl such as $-CH_2CH_2CONHC_6H_5$, or dialkylaminocarbonylalkyl such as $-CH_2CON(CH_3)_2$; cyanoalkyl, for example $-CH_2CN$ or $-CH_2CH_2CN$; alkyl substituted by ether groups, such as alkoxy groups, for example $-CH_2OC_4H_9$ or $-CH_2CH_2OC_8H_{17}$; alkyl substituted by thioether groups, such as alkylthio or arylthio groups, for example $-CH_2CH_2SC_8H_{17}$ or

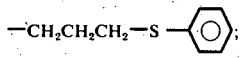

alkyl substituted by sulphoxide groups, such as alkylsulphinylalkyl, for example $-CH_2CH_2SOC_8H_{17}$; alkyl substituted by sulphone groups, such as alkylsulphonylalkyl, for example $-CH_2CH_2CH_2SO_2C_{12}H_{25}$; aminoalkyl, such as aminoalkyl unsubstituted at the nitrogen atom, for example $-CH_2CH_2NH_2$ or $-CH_2CH_2CH_2NH_2$, or such as aminoalkyl substituted by alkyl at the nitrogen atom, for example $-CH_2CH_2-N(CH_3)_2$, $-CH_2CH_2CH_2N(C_2H_5)_2$ or $-CH_2CH_2NHCH_2CH_2CN$.

If X denotes alkenyl it can be, for example, propenyl, butenyl, pentenyl, hexenyl, octenyl, decenyl, tetradecenyl or octadecenyl.

If X denotes alkinyl, it can be, for example, propargyl.

If X is an unsubstituted aralkyl group, it can be benzyl, α-phenylethyl or α, α-dimethylbenzyl.

If X is an aralkyl radical substituted by hydroxyl or ester groups, it can be, for example, 3,5-di-tert.-butyl-4-hydroxybenzyl, 4-propionoxybenzyl or 4-ethoxycarbonylbenzyl.

If X (in the case that $n = 2$) represents an alkylene radical, it can be, for example, methylene, ethylene, trimethylene, tetramethylene, pentamethylene, hexamethylene, heptamethylene, octamethylene, nonamethylene, decamethylene, undecamethylene, dodecamethylene, hexadecamethylene or octadecamethylene.

If the alkylene radical is interrupted by O, NH or S or by groups containing O, N or S, it can be, for example, the following alkylene radicals: radicals interrupted by O or S, such as $-(CH_2)_2-O-(CH_2)_2$, $-(CH_2)_2-S-(CH_2)_2-$, $-CH_2CH_2S(CH_2)_2SCH_2CH_2-$, $-CH_2CH_2S(CH_2)_3SCH_2CH_2-$, $-CH_2CH_2S(CH_2)_4SCH_2CH_2-$, $-CH_2CH_2S(CH_2)_6SCH_2CH_2-$ or $-CH_2CH_2S(CH_2)_{12}SCH_2CH_2-$; radicals interrupted by NH or amino groups, such as $-(CH_2)_2-NH-(CH_2)_2-$, $-(CH_2)_3-NH-(CH_2)_3-$,

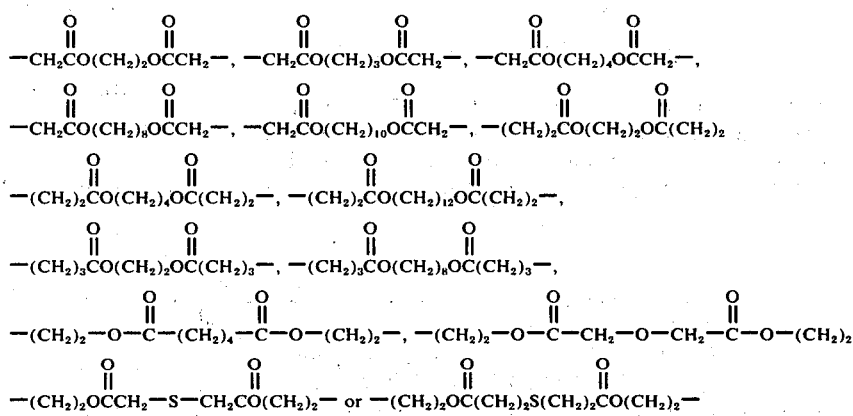

alkylene radicals interrupted by amide groups, such as $-CH_2CONH(CH_2)_2NHCO-CH_2-$, $-CH_2CONH(CH_2)_6NHCOCH_2-$, $-CH_2CONH(CH_2)_{12}NHCOCH_2-$, $-(CH_2)_2CONH(CH_2)_4NHCO(CH_2)_2-$, $-(CH_2)_2CONH(CH_2)_6NHCO(CH_2)_2-$, $-(CH_2)_2CONH(CH_2)_8NHCO(CH_2)_2-$ or $-(CH_2)_3CONH(CH_2)_2NHCO(CH_2)_3-$; radicals interrupted by sulphoxide groups, such as $-(CH_2)_2-SO-(CH_2)_2-$, $-CH_2CH_2-SO-CH_2CH_2-SO-CH_2CH_2-$, $-(CH_2)_2-SO-(CH_2)_{12}-SO-(CH_2)_2-$ or $-CH_2CH_2O-\overset{O}{\underset{\|}{C}}-CH_2-SO-CH_2-\overset{O}{\underset{\|}{C}}-O-CH_2-CH_2-;$ radicals interrupted by sulphone groups such as $-CH_2-CH_2-SO_2-CH_2-CH_2-,$ $-CH_2CH_2-SO_2-(CH_2)_6-SO_2-CH_2CH_2-,$ $-(CH_2)_2-O-\overset{O}{\underset{\|}{C}}-CH_2-SO_2-CH_2-\overset{O}{\underset{\|}{C}}-O-(CH_2)_2-$ or $-(CH_2)_2O-\overset{O}{\underset{\|}{C}}-CH_2CH_2-SO_2-CH_2CH_2-O-\overset{O}{\underset{\|}{C}}-(CH_2)_2-.$ If X denotes alkenylene or alkinylene, it can be, for example, 2-butenylene-1,4, 2-butinylene-1,4 or 2,4-hexadiinylene-1,6.

If X denotes bis(alkylene)arene, it can be 1,2-bis-(methylene)-benzene, 1,3-bis-(methylene)-benzene, 1,4-bis-(methylene)-benzene, 1,2-bis-(ethylene)-benzene, 1,3-bis-(ethylene)-benzene, 1,4-bis-(ethylene)-benzene or 4,4'-bis-(methylene)-diphenyl.

The trivalent hydrocarbon radical T can be, for example, one of the following radicals:

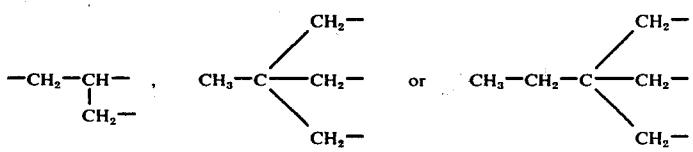

The tetravalent hydrocarbon radical Q can be, for example, the radical

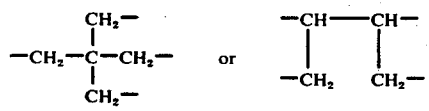

The salts of the compounds of the formula I with organic or inorganic acids can be, for example, salts of acetic acid, formic acid, tartaric acid, phenylphosphonic acid, maleic acid, phosphoric acid, hydrochloric acid, phosphorous acid or carbonic acid.

Preferred compounds of the formula I are those wherein $R_1$, $R_2$, $R_3$ and $R_4$ independently of one another denote alkyl with 1 to 8 C atoms or $R_1$ and $R_2$ and/or $R_3$ and $R_4$ together with the C atom to which they are bonded form a cyclopentyl or cyclohexyl ring, Y denotes hydrogen or the oxyl radical —O·, $n$ denotes an integer from 1 to 4 and X, if $n$ is 1, denotes alkyl with 1 to 20 C atoms, preferably 8 to 18 carbon atoms, which can be substituted by hydroxyl, carboxyl, ester, amide, nitrile, ether, thioether, sulphoxide, sulphone or amino groups, alkenyl or alkinyl with 3 to 18 C atoms or aralkyl with 7 to 15 C atoms, which can be substituted by hydroxyl or ester groups, if $n$ is 2, alkylene with 1 to 12 C atoms, alkylene with 2 to 20 C atoms which is interrupted by ether, ester, thioether, amide, sulphoxide, sulphone or amino groups, alkenylene with 4 to 20 C atoms, alkinylene with 4 to 20 C atoms or bis(alkylene)arene with 8 to 14 C atoms, if $n$ is 3, a group $$-(CH_2)_m-COO-T\begin{matrix}OOC-(CH_2)_m-\\ \\OOC-(CH_2)_m-\end{matrix}$$

in which $m$ represents 1 to 3 and T represents a trivalent aliphatic hydrocarbon radical with 3 to 7 C atoms and if $n$ is 4, a group $$\begin{matrix}-(CH_2)_m-COO\\ \\-(CH_2)_m-COO\end{matrix}\begin{matrix}OOC-(CH_2)_m-\\Q\\OOC-(CH_2)_m-\end{matrix}$$

in which $m$ represents 1 to 3 and Q represents a tetravalent aliphatic hydrocarbon radical with 4 to 5 C atoms, as well as their salts with carboxylic acids or organophosphorus acids with 1 to 20 C atoms.

Compounds of particular interest are those of the formula I wherein $R_1$, $R_2$, $R_3$ and $R_4$ denote alkyl with 1 to 4 c atoms or $R_1$ and $R_2$, and $R_3$ and $R_4$, together with the C atom to which they are bonded form a cyclohexyl ring, Y denotes hydrogen or the oxyl radical —O·, $n$ denotes an integer from 1 to 4 and X, if $n$ is 1, denotes alkyl with 1 to 18 C atoms, which can be substituted by hydroxyl, carboxyl, ester, amide, nitrile, ether, thioether, sulphoxide, sulphone or amino groups, alkenyl or alkinyl with 3 to 5 C atoms, benzyl or benzyl which is substituted by hydroxyl or ester groups, if $n$ is 2, alkylene with 1 to 8 carbon atoms, alkylene with 2 to 12 C atoms which is interrupted by ether, ester, thioether, sulphoxide, sulphone or amino groups, alkenylene or alkinylene with 4 to 6 C atoms or xylylene, if $n$ is 3, a group $$-(CH_2)_m-COO-T\begin{matrix}OOC-(CH_2)_m-\\ \\OOC-(CH_2)_m\end{matrix}$$

in which $m$ represents 1 to 3 and T represents a trivalent aliphatic hydrocarbon radical with 3 to 5 C atoms and if $n$ is 4, a group $$\begin{matrix}-(CH_2)_m-COO\\ \\-(CH_2)_m-COO\end{matrix}\begin{matrix}OOC-(CH_2)_m-\\Q\\OOC-(CH_2)_m-\end{matrix}$$

in which $m$ represents 1 to 3 and Q represents a tetravalent aliphatic hydrocarbon radical with 4 to 5 C atoms, in particular compounds of the formula I, wherein $R_1$ and $R_2$, and $R_3$ and $R_4$, together with the C atom to which they are bonded, each form a cyclohexyl ring, and Y denotes hydrogen or the oxyl radical —O·, $n$ denotes the number 1 or 2 and X, if $n$ is 1, denotes alkyl with 1 to 18 C atoms which can be substituted by ester groups, allyl, methallyl, propargyl or benzyl, and if *n* is 2, denotes alkylene with 2 to 4 C atoms or alkylene with 6 to 10 C atoms which is interrupted by ester groups.

Examples of specific compounds of the formula I are: 14-(butyl)-7,14-diaza-15-oxo-dispiro[5.1.5.2]pentadecane, 14-(octyl)-7,14-diaza-15-oxo-dispiro[5.1.5.2]pentadecane, 14-(octadecyl)-7,14-diaza-15-oxo-dispiro[5.1.5.2]pentadecane, 14-(octadecyl)-7,14-diaza-15-oxo-dispiro[5.1.5.2]pentadecane-7-oxyl, 14-(2'-phenyl-2'-hydroxyethyl)-7,14-diaza-15-oxo-dispiro[5.1.5.2]-pentadecane, 14-(carboxymethyl)-7,14-diaza-15-oxo-dispiro[5.1.5.2]-pentadecane, 14-(methoxycarbonylmethyl)-7,14-diaza-15-oxo-dispiro[5.1.5.2]-pentadecane, 14-(octyloxycarbonylmethyl)-7,14-diaza-15-oxo-dispiro[5.1.5.2]-pentadecane, 14-(octadecyloxycarbonylmethyl)-7,14-diaza-15-oxo-dispiro[5.1.5.2]-pentadecane, 14-(methoxycarbonylethyl)-7,14-diaza-15-oxo-dispiro[5.1.5.2]-pentadecane, 14-(ethoxycarbonylethyl)-7,14-diaza-15-oxo-dispiro[5.1.5.2]-pentadecane, 14-(octyloxycarbonylethyl)-7,14-diaza-15-oxo-dispiro[5.1.5.2]-pentadecane, 14-(octadecyloxycarbonylethyl)-7,14-diaza-15-oxo-dispiro[5.1.5.2]pentadecane, 14-(2'-phenyl-2'-acetoxyethyl)-7,14-diaza-15-oxo-dispiro[5.1.5.2]pentadecane, 14-(acetamidoethyl)-7,14-diaza-15-oxo-dispiro[5.1.5.2]pentadecane, 14-(cyanomethyl)-7,14-diaza-15-oxo-dispiro[5.1.5.2]pentadecane, 14-(octyloxethyl)-7,14-diaza-15-oxo-dispiro[5.1.5.2]pentadecane, 14-(octylthioethyl)-7,14-diaza-15-oxo-dispiro[5.1.5.2]pentadecane, 14-(octylsulphinylethyl)-7,14-diaza-15-oxo-dispiro[5.1.5.2]pentadecane, 14-(octylsulphonylethyl)-7,14-diaza-15-oxo-dispiro[5.1.5.2]-pentadecane, 14-(allyl)-7,14-diaza-15-oxo-dispiro[5.2.5.2]-pentadecane, 14-(methallyl)-7,14-diaza-15-oxo-dispiro[5.1.5.2]-pentadecane, 14-(propargyl)-7,14-diaza-15-oxo-dispiro[5.1.5.2]-pentadecane, 14-(benzyl)-7,14-diaza-15-oxo-dispiro[5.1.5.2]-pentadecane, 14-(benzyl)-7,14-diaza-15-oxo-dispiro[5.1.5.2]-pentadecan-7-oxyl, 1',2'-bis(7,14-diaza-15-oxo-dispiro[5.1.5.2]pentadecyl-14)-ethane, 1',4'-bis(7,14-diaza-15-oxo-dispiro[5.1.5.2]pentadecyl-14)-n-butane, 1',8'-bis(7,14-diaza-15-oxo-dispiro[5.1.5.2]pentadecyl-14)-n-octane, ethylene-di(7,14-diaza-15-oxo-dispiro[5.1.5.2]pentadecyl-14)-acetate, tetramethylene-di(7,14-diaza-15-oxo-dispiro[5.1.5.2]pentadecyl-14)acetate, octamethylene-di(7,14-diaza-15-oxo-dispiro[5.1.5.2]pentadecyl-14)acetate, octadecylmethylene-di(7,14-diaza-15-oxo-dispiro[5.1.5.2]pentadecyl-14)acetate, ethylene-di-α-(7,14-diaza-15-oxo-dispiro[5.1.5.2]pentadecyl-14)propionate, tetramethylene-di-γ-(7,14-diaza-15-oxo-dispiro[5.1.5.2]pentadecyl-14)butyrate, N,N'-ethylene-bis[(7,14-diaza-15-oxo-dispiro[5.1.5.2]pentadecyl-14)acetamide], 1',6'N,N'-hexamethylene-bis[(7,14-diaza-15-oxo-dispiro[5.1.5.2]pentadecyl-14)acetamide], 1',4'-bis(7,14-diaza-15-oxo-dispiro[5.1.5.2]pentadecyl-14)butene-2',1',4'-bis(7,14-diaza-15-oxo-dispiro[5.1.5.2]pentadecyl-14)butine-2', bis(7,14-diaza-15-oxo-dispiro[5.1.5.2]pentadecyl-14)-o-xylylene, bis(7,14-diaza-15-oxo-dispiro[5.1.5.2]pentadecyl-14)-m-xylylene, bis(7,14-diaza-15-oxo-dispiro[5.1.5.2]pentadecyl-14)-p-xylylene, tris(7,14-diaza-15-oxo-dispiro[5.1.5.2]pentadecyl-14-acetoxy)-propane-1', 2', 3', tris(7,14-diaza-15-oxo-dispiro[5.1.5.2]pentadecyl-14-propionoxy)propane-1',2',3', tetrakis(7,14-diazo-15-oxo-dispiro[5.1.5.2]pentadecyl-14-propionoxymethyl)methane, 3-butyl-2,2,5,5-tetramethyl-4-oxo-imidazolidine, 3-octyl-2,2,5,5-tetramethyl-4-oxo-imidazolidine, 3-octadecyl-2,2,5,5-tetramethyl-4-oxo-imidiazolidine, 3-(2'-phenyl-2'-hydroxyethyl)-tetramethyl-4-oxo-imidazolidine, 3-carboxymethyl-2,2,5,5-tetramethyl-4-oxo-imidazolidine, 3-butyloxycarbonylmethyl-2,2,5,5-tetramethyl-4-oxo-imidazolidine, 3-octyloxycarbonylmethyl-2,2,5,5-tetramethyl-4-oxo-imidazolidine, 3-ethoxycarbonylethyl-2,2,5,5-tetramethyl-4-oxo-imidazolidine, 3-octyloxycarbonylethyl-2,2,5,5-tetramethyl-4-oxo-imidazolidine, 3-(2'-phenyl-2'-acetoxy-ethyl)-2,2,5,5-tetramethyl-4-oxo-imidazolidine, 3-cyanoethyl-2,2,5,5-tetramethyl-4-oxo-imidazolidine, 3-allyl-2,2,5,5-tetramethyl-4-oxo-imidazolidine, 1',2'-bis(2,2,5,5-tetramethyl-4-oxo-imidazolidinyl-3-)ethane, 1',4'-bis(2,2,5,5-tetramethyl-4-oxo-imidazolidinyl-3-)n-butane, 1',8'-bis(2,2,5,5-tetramethyl-4-oxo-imidazolidinyl-3-(n-octane, ethylene-di(2,2,5,5-tetramethyl-4-oxo-imidazolidinyl-3-acetate), 1',8'-octylene-di(2,2,5,5-tetramethyl-4-oxo-imidazolidinyl-3-acetate), N,N'-ethylene-bis[(2,2,5,5-tetramethyl-4-oxo-imidazolidinyl-3-)acetamide], 1',6'N,N'-hexamethylene-bis[2,2,5,5-tetraamethyl-4-oxo-imidazolidinyl-3-)acetamide], 1',4'-bis-(2,2,5,5-tetramethyl-4-oxo-imidazolidinyl-3-)2'-butene, 1',4'-bis(2,2,5,5-tetramethyl-4-oxo-imidazolidinyl-3-)2'-butine, bis(2,2,5,5-tetramethyl-4-oxo-imidazolidinyl-3-)-o-xylylene, tris(2,2,5,5-tetramethyl-4-oxo-imidazolidinyl-3-acetoxy)propane-1',2',3', tris(2,2,5,5-tetramethyl-4-oxo-imidazolidinyl-3-acetoxymethyl)-ethane-1',1',1', tetrakis(2,2,5,5-tetramethyl-4-oxo-imidazolidinyl-3-acetoxy-methyl)methane.

The compounds according to the invention, of the formula I, can be manufactured by reacting 4-oxo-imidazolidines of the formula II

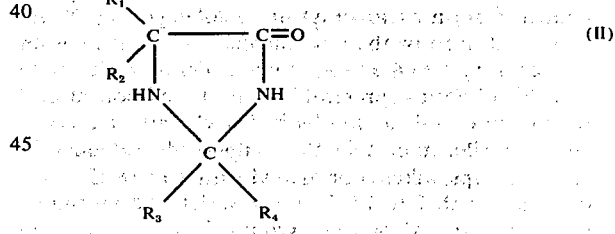

with alkylating agents and optionally (a) oxidising the compounds of the formula I, thus obtained, wherein Y is hydrogen, and the remaining symbols have the meaning indicated initially, to compounds of the formula I in which Y represents the oxyl radical, or optionally (b) converting compounds of the formula I thus obtained, wherein Y is hydrogen and the remaining symbols have the meaning indicated initially, into the corresponding salts by treatment with organic or inorganic acids.

The 4-oxo-imidazolidines of the formula II used as the starting material are known substances which can be prepared, for example, by the processes described in Journal of Organic Chemistry 28 (1963), 3576 or in German Offenlegungsschrift 1,817,703. Preferred starting materials are those compounds of the formula II in which $R_1$, $R_2$, $R_3$ and $R_4$ independently of one another denote alkyl with 1 to 8 C atoms, especially with 1 to 4 C atoms, or in which $R_1$ and $R_2$ and/or $R_3$ and $R_4$ together with the C atom to which they are bonded form a cyclopentyl or cyclohexyl ring, but especially a cyclohexyl ring.

Examples of such compounds of the formula II, suitable for use as starting materials, are: 2,2,5,5-tetramethyl-4-oxo-imidazolidine, 2,2,5,5-tetra-n-butyl-4-oxo-imidazolidne, 2,5-dimethyl-2,5-diisopropyl-4oxo-imidazolidine, 2,5-dimethyl-2-isopropyl-5-ethyl-4-oxo-imidazolidine, 7,14-diaza-15-oxo-dispiro[5.1.5.2]pentadecane, 6,12-diaza-13-oxo-dispiro[4.1.4.2]tridecane and 8,8-dimethyl-7,9-diaza-10-oxo-spiro[5.4]decane.

The conversion of the imidazolidones of the formula II to the compounds of the formula I, wherein Y is hydrogen, is carried out according to known methods oa alkylation, with known alkylating agents.

The most versatile method is the reaction with organic halogen compounds of the formula X-Hal$_n$, wherein Hal denotes chlorine, bromine or iodine and X and $n$ have the abovementioned meaning, in the presence of molar amounts of a deprotonising agent, or after deprotonising the imidazolidones with molar amounts of such an agent. As deprotonising agent it is possible to use alkali metals, alkali metal hydrides, alkali metal hydroxides, alkali metal amides or similar reactive alkali metal compounds. Alkaline earth metal compounds such as calcium hydride can also be used. As examples of halogen compounds X-Hal$_n$ which can be used according to the invention there may be mentioned: methyl iodide, ethyl bromide, n-propyl bromide, 1-n-dodecyl bromide, ethylene chlorohydrin, propionic acid chloroethyl ester, hexahydrobenzoic acid 2-chloroethyl ester, chloroacetic acid, sodium chloroacetate, ethyl chloroacetate, chloracetamide, N-dimethylchloroacetamide, chloroacetanilide, chloroacetonitrile, 1-β-chloroethoxy-n-octane, 1-β-bromoethylmercaptobutane, allyl chloride, oleyl bromide, propargyl chloride, benzyl chloride, β-phenylethyl bromide, 3,5-di-tert.-butyl-4-hydroxybenzyl chloride, 4-chloromethyl-benzoic acid ethyl ester, 1,2-dibromoethane, tetramethylene dibromide, dodecamethylene diiodide, 2,2'-dichlorodiethyl ether, ethylene glycol bis-(2-chloroethyl ether), bis-(2-chloroethyl)-2-cyanoethylamine, ethylene di(chloroacetate), hexamethylene di(bromoacetate), adipic acid di(2-chloroethyl ester), diglycollic acid di(2-chloroethyl ester), thiodipropionic acid di(2-chloroethyl ester), sulphonedipropionic acid di(2-chloroethyl ester), hexamethylene-bis(chloroacetamide), 1,4-dichlorobutene-2, 1,4-dichlorobutine-2, 1,6-dichlorohexadiine-2,4, o-, m- or p-xylylene dichloride, glycerine tri(chloroacetate), trimethylolpropane tri(chloroacetate) and pentaerythritol tetra(chloroacetate).

The reaction is preferably carried out in organic solvents such as, for example, in benzene, toluene, dimethylformamide, dimethylsulphoxide or their mixtures.

A possible method of alkylating the imidazolidones while introducing a hydroxyalkyl group consists of reacting them with formaldehyde to give the hydroxmethyl compounds or of reacting them with epoxides to give the 2-hydroxylalkyl compounds. Examples of such epoxides are ethylene oxide, propylene oxide or styrene oxide.

If the reaction with formaldehyde is carried out in the presence of an alcohol, the corresponding alkoxymethyl derivatives are formed; for example, the N-butoxymethyl derivative is formed in the presence of butanol.

One method of alkylation for the introduction of aminoalkyl groups consists of the reaction of the imidazolidones with formaldehyde and amines or their salts, preferably with secondary amines such as, for example, dimethylamine, diethylamine or their salts.

A further important method for the introduction of substituted alkyl groups is the addition of α,β-unsaturated carboxylic acid derivatives. Acrylonitrile, acrylic acid esters and acrylamide can, above all, be added on to the imidazolidones of the formula II, using alkaline catalysis. Vinylsulphones and vinylsulphoxides, for example vinyl-benzylsulphone or divinylsulphone can also be added on under these conditions.

Some of the substituted imidazolidine derivatives obtained by such alkylation reactions can be converted into other imidazolidine derivatives of the formula I with Y = H according to known methods, by a further reaction stage. Thus, for example, the 3-cyanoethyl derivatives can be converted into the 3-aminopropyl derivatives by hydrogenation. The hydroxyalkyl compounds can be esterified to the acyloxyalkyl compounds with carboxylic acids. Thioether compounds can be oxidised to the sulphoxides or the sulphones and ester compounds can be hydrolysed to the free carboxyl compounds.

The imidazolidine compounds of the formula I, thus obtainable, which are substituted in the 3-position and in wich Y = H, can be converted into the corresponding nitroxyls of the formula I, in which Y represents the oxyl radical. This takes place according to known methods, for example by oxidation with hydrogen peroxide and sodium tungstate in an aqueous medium or by oxidation with a percarboxylic acid such as, for example, peracetic acid or m-chloroperbenzoic acid in organic solvents.

Since the imidazolidine derivatives according to the invention are basic compounds, they are able to form salts with organic or inorganic acids. The salt formation takes place according to known methods by addition of the corresponding acid in stoichiometric amounts or in excess amounts, before, during or after the manufacture of the compounds of the formula I. Acids which are suitable for this purpose are, for example, acetic acid, formic acid, tartaric acid, phenylphosphonic acid, maleic acid or phosphoric acid.

The physical properties of the compounds according to the invention, of the formula I, differ greatly depending on the individual substituents, above all depending on the substituent X. However, all compounds of the formula I, when added even in small amounts, are capable of protecting organic polymers against aging through the action of light. The light aging of organic polymers can on the one hand lead to degradation and deterioration of the mechanical properties, associated therewith, and, on the other hand, to a discolouration of the polymers. Both aging phenomena can also occur alongside one another.

The compounds according to the invention now protect organic polymers against both the adverse phenomena of light aging and, surprisingly, do so substantially more effectively than the known starting compounds of the formula II are able to do.

Polymers of which the light aging can be delayed or prevented by the compounds of the formula I according to the invention are, for example, the following categories which are industrially important.

1. Polymers which are derived from singly or doubly unsaturated hydrocarbons, for example, polyolefines such as polyethylene, which an optionally be crosslinked, polypropylene, polybutene-1, polyisobutene, polymethylbutene-1, polymethylpentene-1, polyisoprene, polybutadiene, polystyrene, copolymers of the monomers on which the homopolymers mentioned are based, such as ethylene-propylene copolymers, propylene-butene-1 copolymers, propylene-isobutene copolymers, styrene-butadiene copolymers and terpolymers of ethylene and propylene with a diene such as, for example, hexadiene, dicyclopentadiene or ethylidenenorbornene; mixtures of the abovementioned homopolymers such as, for example, mixtures of polypropylene and polyethylene, polypropylene and polybutene-1 or polypropylene and polyisobutylene, or of butadiene-acrylonitrile copolymer with a styrene-butadiene copolymer.

2. Vinyl polymers conaining halogen such as polyvinyl chloride, polyvinylidene chloride, polyvinyl fluoride, polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, stearate, benzoate and maleate, polyvinyl butyral, polyallyl phthalate, polyallylmelamine and their copolymers with other vinyl compounds such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as polyoxymethylenes which contain ethylene oxide as a comonomer.

7. polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polayamide 11 and polyamide 12.

12. Polyesters which are derived from dicarboxylic acids and dialcohols and/or from hydroxycarboxylic acids or the corresponding lactones, such as polyethylene glycol terephthalate, polybutylene terephthalate, poly-1,4-dimethylol-cyclohexane terephthalate and their starting materials, such as lower terephthalic acid alkyl esters.

13. Crosslinked polymers which are derived from aldehyes, on the one hand, and phenols, ureas and melamines, on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters or saturated and unsaturated dicarboxylic acids with polyhydric alcohols, and vinyl compounds as crosslinking agents, and also their halogen-containing modifications of low flammability.

16. Natural polymers, such as cellulose, rubber, proteins, and their polymer-homologously chemically modified derivatives, such as cellulose acetates, propionates and butyrates, or the cellulose ethers, such as methylcellulose.

Preferred polymers are polyethylene of high and low density, polypropylene, polybutadiene, polyvinyl chloride, polystyrene and its copolymers and mixtures thereof.

The new compounds are added to the substrates in a concentration of 0.01 to 5% by weight, calculated relative to the material to be stabilised. Preferably, 0.05 to 1.5, and especially preferentially 0.1 to 0.8, % by weight of the compounds, calculated relative to the material to be stabilised, are incorporated into the latter.

The incorporation can be effected after the polymerisation, for example by mixing the compounds and optionally further additives into the melt in accordance with the industrially customary methods, before or during shaping, or by applying the dissolved or dispersed compounds to the polymer, if necessary with subsequent evaporation of the solvent.

The new compounds can also be added to the polymers to be stabilised in the form of a master batch which contains these compounds, for example, in a concentration of 2.5 to 25% by weight.

In the case of crosslinked polyethylene, the compounds are added before crosslinking.

The following may be mentioned as further additives together with which the stabilisers usable according to the invention can be employed:

1. Antioxidants 1.1 Simple 2,6-dialkylphenols such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl)-phosphite, 3,5-di-tert.-butyl-4-hydroxyphenyl-stearate and bis-(3,5-di-tert.-butyl-4-hydroxyphenyl)-adipate.

1.3 Hydroxylated thiodiphenyl ethers such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4 Alkylidene-bisphenols such as, for example, 2,2'-methylene-bis-(6-tert.butyl-4-methylphenol),2,2'-methylene-bis-(6-tert.butyl-4-ethylphenol), 4,4'-methylene-bis-(6-tert. butyl-2-methylphenol), 4,4'-methylene-bis-(2,6-di-tert. butyl-phenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert. butyl-4-hydroxy-2-methylphenyl)-4-n-dodecylmercaptobutane, 1,1,5,5-tetra-(5-tert.butyl-4-hydroxy-2-methylphenyl)-pentane and ethylene-glycol-bis-[3,3-bis-(3'-tert.butyl-4'-hydroxyphenyl)-butyrate].

1.5 O-, N- and S-benzyl compounds such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis-(4-tert.butyl-3-hydroxy-2,6-dimethylbenzyl)-dithiol terephthalate.

1.6 Hydroxybenzylated malonic esters such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert. butyl-4-hydroxybenzyl)-malonic acid di-dodecylmercapto ethylester and 2,2-bis-(3,5-di-tert.butyl-4-hydroxybenzyl)malonic acid di-[4-(1,1,3,3-tetramethylbutyl)-phenyl]-ester.

1.7 Hydroxybenzyl-aromatics such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds such as, for example, 2,4-bis-octylmercapto-6-(3,5-di-tert.butyl-4-hydroxy-anilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example, 1,3,3-tri-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]octane.

1.11. Esters of β-(5-tert.butyl-4-hydroxy-3-methylphenylpropionic acid with monohydric or polyhydric alcohols such as, for example, methanol, ethanol, octadecanol, 1,6-hexanediol, 1,9-nonanediol, ethylene glycol; 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.12. Esters of 3,5-di-tert.butyl-4-hydroxyphenylacetic acid with monohydric or polyhydric alcohols such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.13. Acylaminophenols such as, for example, N-(3,5-di-tert. butyl-4-hydroxyphenyl)-stearic acid amide and N,N'-di-(3,5-di-tert.butyl-4-hydroxyphenyl)-thiobisacetamide.

1.14. Benzylphosphonates such as, for example, 3,5-di-tert. butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-disec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline.

2. UV absorbers and light protection agents:

2.1. 2-(2'-Hydroxyphenyl)-benztriazoles, such as, for example, the 5'-methyl-, 3',5'-di-tert.butyl-, 5'-tert.butyl-, 5'-(1,1, 3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert. amyl-, 3'-methyl-5'-carbomethoxyethyl- and 5-chloro-3',5'-di-tert.amyl-derivative.

2.2. 2,4-Bis-(2'-hydroxyphenyl)-6-alkyl-s-triazines, such as, for example, the 6-ethyl-, 6-heptadecyl or 6-undecyl-derivative.

2.3. 2-Hydroxy-benzophenones, such as, for example, the 4-hydroxy-, 4-methoxy-, 4-octoxy-, 4-decyloxy-, 4-dodecyloxy-, 4-benzyloxy, 4,2',4'-trihydroxy- or 2'-hydroxy-4,4'-dimethoxy-derivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids such as, for example, phenyl salicylate, octylphenyl salicylate, di-benzoylresorcinol, bis-(4-tert.butylbenzoyl)-resorcinol, benzoylresorcinol and 3,5-di-tert.butyl-4-hydroxybenzoic acid 2,4-di-tert.butyl-phenyl ester, octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as the methyl, ethyl or butyl ester, nickel complexes of ketoximes such as of 2-hydroxy-4-methyl-phenyl-undecylketonoxime and nickel 3,5-di-tert.butyl-4-hydroxy-benzoate.

2.8. Sterically hindered amines, such as, for example, 4-benzoyloxy-2,2,6,6-tetramethylpiperidine, 4- stearoyloxy-2,2,6,6-tetramethylpiperidine, bis-(2,2,6,6-tetramethylpiperidyl)-sebacate, and 3-n-octyl-7,7,9,9-tetramethyl-1,3,8-triaza-spiro[4,5]decane-2,4-dione.

2.9. Oxalic acid diamides, such as, for example, 4,4′-di-octyloxy-oxanilide, 2,2′-di-octyloxy-5,5′-di-tert.butyl-oxanilide, 2,2′-di-dodecyloxy-5,5′-di-tert.butyl-oxanilide, 2-ethoxy-2′-ethyl-oxanilide, N,N′-bis-(3-dimethylaminopropyl)-oxalamide, 2-ethoxy-5-tert.butyl-2′-ethyl-oxanilide and its mixture with 2-ethoxy-2′-ethyl-5,4′-di-tert. butyl-oxanilide, mixtures of ortho- and para-methoxy- as well as of o- and p-ethoxy-disubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N′-diacetyl-adipic acid dihydrazide, N,N′-bis-salicyloyloxalic acid dihydrazide, N,N′-bis-salicyloylhydrazine and N,N′-bis-(3,5-di-tert.butyl-4-hydroxyphenyl-propionyl)hydrazine.

4. Phosphites, such as, for example, triphenylphosphite, diphenylalkylphosphites, phenyldialkylphosphites, tri-(nonylphenyl)-phosphite, trilaurylphosphite, trioctadecylphosphite, 3,9-di-isodecyloxy-2,4,8,10-tetraoxa-3,9-diphosphaspiro[5.5]undecane and tri-(4-hydroxy-3,5-di-tert.butylphenyl)-phosphite.

5. Compounds which destroy peroxides, such as, for example, esters of β-thiodipropionic acid, for example the lauryl, stearyl, myrystyl or tridecyl esters, salts of 2-mercaptobenzimidazole, for example the Zn salt, and diphenylthiourea.

6. Polyamide stabilisers, such as, for example, copper salts in combination with iodides and/or phosphorus compounds and salts of divalent manganese.

7. Basic co-stabilisers, such as, for example, melamine, benzoguanamine, polyvinylpyrrolidone, dicyandiamide, triallyl-cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate.

8. PVC stabilisers, such as, for example, organic tin compounds, organic lead compounds and barium-cadmium salts of fatty acids.

9. Nucleating agents, such as for example 4-tert.butylbenzoic acid, adipic acid and diphenylacetic acid.

10. Other additives, such as, for example, plasticisers, lubricants, emulsifiers, fillers, carbon black, asbestos, kaolin, talc, glass fibres, pigments, optical brighteners, flameproofing agents and antistatic agents.

The manufacture and use of the compounds according to the invention is described in more detail in the examples which follow. In these, parts denote parts by weight.

EXAMPLE 1

4.3 g (0.1 mol) of a 55–60% strength dispersion of sodium hydride in toluene are added to 22.2 g (0.1 mol) of 7,14-diaza-15-oxo-dispiro[5.1.5.2]pentadecane (manufactured according to Journal of Org. Chem. 28, (1963), 3576) in 200 ml of toluene and the mixture is kept under reflux for 20 hours. A solution of 12.6 g (0.1 mol) of benzyl chloride in 200 ml of dimethylformamide is then added dropwise and the mixture is kept under reflux for a further 12 hours. It is cooled, the NaCl formed is filtered off, the filtrate is evaporated and the residue is recrystallised from hexane. 14-Benzyl-7,14-diaza-15-oxo-dispiro[5.1.5.2]pentadecane (I) of melting point 115°C is obtained.

EXAMPLES 2 TO 6

The procedure of Example 1 is followed but instead of the benzyl chloride used there, 0.1 mol of the alkylating agents listed in column 1 of Table 1 are used and the products listed in column 2 are obtained.

Table I

Alkylation of 7,14-diaza-15-oxo-dispiro[5.1.5.2]pentadecane with halogen compounds

| Halogen compound used | Product obtained | Substance No. | Melting point/ boiling point |
|---|---|---|---|
| Allyl chloride | 14-Allyl-7,14-diaza-15-oxo-dispiro[5.1.5.2]pentadecane | II | Boiling point 128°C at 0.06 mm Hg |
| Octyl bromide | 14-Octyl-7,14-diaza-15-oxo-dispiro[5.1.5.2]pentadecane | III | Boiling point 181°C at 0.5 mm Hg |
| Octadecyl bromide | 14-Octadecyl-7,14-diaza-15-oxo-dispiro[5.1.5.2]-pentadecane | IV | Melting point 45°C |
| Methyl bromoacetate | 14-Methoxycarbonylmethyl-7,14-diaza-15-oxo-dispiro-[5.1.5.2]pentadecane | V | Melting point 90°C |
| 0.05 mol of 1,4-dibromobutane | 1′,4′-Bis(7,14-diaza-15-oxo-dispiro[5.1.5.2]pentadecyl-14)butane | VI | Melting point 155–156°C |

EXAMPLE 7

If, instead of 7,14-diaza-15-oxo-dispiro[5.1.5.2]pentadecane, 2,2,5,5-tetramethyl-4-oxo-imidazolidine is used, and this alkylated with benzyl chloride as described in Example 1, then 3-benzyl-2,2,5,5-tetramethyl-4-oxo-imidazolidine (VII), M.P. 210°C, is obtained.

EXAMPLE 8

29.5 parts by weight (0.1 mol) of 14-methoxycarbonylmethyl-7,14-diaza-15-oxo-dispiro[5.1.5.2]pentadecane (V), 13 g (0.1 mol) of 1-octanol and 25 ml of xylene are warmed to 130°C. On adding 0.2 g of $LiNH_2$, the evolution of methanol immediately commences. After half an hour, the temperature is raised to 140°C and is maintained thereat until no further methanol or xylene distils off. The mixture is cooled and 0.7 ml of glacial acetic acid is added. After taking up the product in toluene, washing the organic phase with water, drying it with sodium sulphate and stripping off the solvent in vacuo, 14-octyloxycarbonylmethyl-7,14-diaza-15-oxo-dispiro[5.1.5.2]pentadecane (VII) is obtained as an oily residue, the analysis and infrared spectrum of which agree with the above structure.

EXAMPLES 9 to 11

If corresponding polyols are used, with the procedure otherwise according to Example 7, then there are obtained the products given in column 2 of Table 2.

Table 2

Transesterification of 14-methoxycarbonylmethyl-7,14-diaza-15-oxo-dispiro-[5.1.5.2]pentadecane with polyols.

| Employed polyol | Product obtained | Substance No. | M.P. B.P. |
|---|---|---|---|
| ethylene glycol | ethylene-di-(7,14-diaza-15-oxo-dispiro[5.1.5.2]pentadecyl-14-acetate) | IX | 150°C |
| 1,1,1-tris-(hydroxymethyl)-ethane | tris(7,14-diaza-15-oxo-dispiro[5.1.5.2]pentadecyl-14-acetoxymethyl)-ethane-1',1',1' | X | 100–110°C |
| pentaerythritol | tetrakis(7,14-diaza-15-oxo-dispiro[5.1.5.2]pentadecyl-14-acetoxymethyl)methane | XI | 50°C |

EXAMPLE 12

7.61 g of m-chloroperbenzoic acid, dissolved in 150 ml of methylene chloride is added dropwise over the course of 3.5 hours to 9.7 g (0.02 mol) of 14-octadecyl-7,14-diaza-15-oxo-dispiro [5.1.5.2]pentadecane, dissolved in 100 ml of methylene chloride. The reaction is slightly exothermic. The mixture is then stirred for a further 15 hours at room temperature and the m-chlorobenzoic acid which has precipitated is filtered off. The reddish-coloured methylene chloride solution is washed twice with 50 ml of 2 N sodium hydroxide solution at a time and then with 50 ml of 2 N hydrochloric acid and is dried over sodium sulphate. After distilling off the solvent, the residue is crystallised from ethanol. 14-Octadecyl-7,14-diaza-15-oxo-dispiro[5.1.5.2]pentadecane-7-oxyl (XII) of the formula

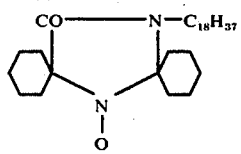

of melting point 34°–35°C is obtained.

EXAMPLE 13

100 parts of polypropylene powder (Moplen, fibre grade, from Messrs. Montedison) are homogenised with 0.2 part of β-(3,5-di-tert-butyl-4-hydroxyphenyl)-propionic acid octadecyl ester as the antioxidant and 0.25 part of a light stabilizer from Table 2 below, for 10 minutes in a Brabender plastograph at 200°C. The mass thus obtained is taken from the kneader as rapidly as possible and is pressed in a toggle press to give 2 - 3 mm thick sheets. A part of the pressed blank obtained is cut out and pressed between two high gloss hard aluminium foils for 6 minutes at 260°C and 12 tons pressure, using a manual hydraulic laboratory press, to give an 0.5 mm thick film which is immediately chilled in cold water. The 0.1 mm thick test film is produced from this 0.5 mm film under exactly the same conditions. Pieces of 60 × 44 mm are now punched from the 0.1 mm thick film and exposed in the Xenotest 150. At regular intervals of time, these test specimens are taken from the light exposure apparatus and examined for their carbonyl content in an IR-spectrophotometer. The increase in the carbonyl extinction during exposure to light is a measure of the photo-oxidative degradation of the polymer [see L. Balabán et al., J. Polymer Sci. Part C, 22, 1059–1071 (1969); J. F. Heacock, J. Polymer Sci. Part A-1, 22, 2921–34 (1969); D. J. Carlsson and DM. Wiles, Macromolecules 2,587–606 (1969)] and is, according to experience, associated with a deterioration of the mechanical properties of the polymer. Thus, for example, the film stabilised with antioxidant only is completely brittle when it reaches a carbonyl extinction of approx. 0.300. The protective action of the light stabilizers according to the invention can be seen from the following Table 3:

Table 3

| Substance No. | Exposure time in hours, | CO extinction (5.85 μ) |
|---|---|---|
| No light stabilizer | 1,000 | 0.300 |
| I | 6,000 | 0.010 |
| VI | 6,000 | 0.010 |
| VII | 5,000 | 0.010 |
| XI | 5,000 | 0.010 |

EXAMPLE 14

100 parts of polystyrene granules are mixed dry with 0.25 part of a light stabilizer from Table 4 below and the mixture is regranulated in an extruder and subsequently moulded on an injection moulding machine to give 2 mm thick sheets. The sheets obtained are exposed for 2,000 hours in the Xenotest 150 apparatus and their yellowing is determined as follows, from the yellowing factor:

$$\text{Yellowing factor } (Y.F.) = \frac{\Delta T(420) - \Delta T(680)}{T(560)} \times 100$$

wherein $\Delta T$ denotes the loss in transmission at wavelengths 420 and 680 nm respectively, which has occurred during exposure, and $T(560)$ denotes the transmission value in percent of the unexposed sample at 560 nm.

Table 4

| Substance No. | Y.F. |
|---|---|
| No light stablizer | 20.0 |
| I | 4.5 |
| VI | 5.5 |

EXAMPLE 15

100 Parts of polyethylene having a density of 0.917 are homogeneously mixed in a Brabender plastograph with 0.1 and 0.3 parts, respectively, of a light-stabilising agent of formula I at 180°C for 10 minutes. The resulting mixture is moulded in a platen press at 170°C to give 1 mm thick sheets, and these are then examined visually for undissolved constituents. The sheets are suspended at room temperature and periodically examined for efflorescence phenomena. The results are shown in Table 5.

Table 5

| Substance No. | Solubility | | Compatibility* | |
|---|---|---|---|---|
| | 0.1% | 0.3% | 0.1% | 0.3% |
| 7,14-diaza-15-oxo-dispiro[5.1.5.2]pentadecane | not dissolved | not dissolved | | |
| II | dissolv. | dissolv. | 200 | 200 |
| III | dissolv. | dissolv. | 200 | 200 |
| IV | dissolv. | dissolv. | 200 | 200 |
| VIII | dissolv. | dissolv. | 200 | 200 |

*Compatibility: number of days over which no efflorescence phenomena are detectable.

What we claim is:
1. Compounds of the formula

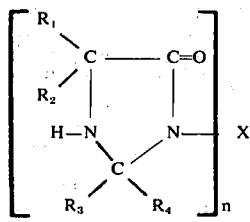

wherein $R_1$ and $R_2$ and $R_3$ and $R_4$, together with the carbon atoms to which they are bonded, form cycloalkyl radicals, $n$ is an integer of 1 or 2, and X, if $n$ is 1, is an alkyl group of 8 to 18 carbon atoms, allyl, methallyl, propargyl or benzyl group, and if $n$ is 2, an alkylene group with 2 to 4 carbon atoms or alkylene with 2 to 10 carbon atoms which is interrupted by ester groups.

2. A compound of claim 1 wherein $n$ is 1.
3. A compound of claim 1 wherein $n$ is 2.
4. The compound of claim 1 which is 14-benzyl-7,14-diaza-15-oxo-dispiro [5.1.5.2]pentadecane.
5. The compound 14-allyl-7,14-diaza-15-oxo-dispiro [5.1.5.2]pentadecane.
6. The compound 14-octyl-7,14-diaza-15-oxo-dispiro [5.1.5.2]pentadecane.
7. The compound 14-octadecyl-7,14-diaza-15-oxo-dispiro [5.1.5.2]pentadecane.
8. The compound 1',4'-bis (7,14-diaza-15-oxo-dispiro [5.1.5.2]pentadecyl-14) butane.
9. An organic polymer stabilized with 0.01 to 5% of a compound of claim 1.
10. A composition of claim 9 wherein the organic polymer is polyolefine.
11. A composition of claim 9 wherein the organic polymer is a copolymer of butadiene.
12. A composition of claim 9 wherein the organic polymer is polystyrene or a styrene copolymer.

* * * * *